(12) United States Patent
Ghelmansarai

(10) Patent No.: US 7,263,165 B2
(45) Date of Patent: Aug. 28, 2007

(54) FLAT PANEL DETECTOR WITH KV/MV INTEGRATION

(75) Inventor: Farhad Ghelmansarai, Danville, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 228 days.

(21) Appl. No.: 11/182,329

(22) Filed: Jul. 14, 2005

(65) Prior Publication Data

US 2007/0025513 A1    Feb. 1, 2007

(51) Int. Cl.
*H05G 1/64* (2006.01)
*G01N 23/04* (2006.01)

(52) U.S. Cl. ............... 378/98.8; 378/62; 378/98.9; 250/370.09; 250/370.11

(58) Field of Classification Search ............... 378/62, 378/98.8, 98.9; 250/370.09, 370.11
See application file for complete search history.

(56) References Cited

U.S. PATENT DOCUMENTS

| | | | |
|---|---|---|---|
| 6,841,784 B2 * | 1/2005 | Brahme et al. | 250/370.08 |
| 6,888,919 B2 * | 5/2005 | Graf | 378/65 |
| 6,895,077 B2 * | 5/2005 | Karellas et al. | 378/98.3 |
| 2006/0113497 A1 * | 6/2006 | Sommer | 250/503.1 |
| 2006/0214109 A1 * | 9/2006 | Bueno et al. | 250/370.11 |

* cited by examiner

*Primary Examiner*—Edward J. Glick
*Assistant Examiner*—Thomas R. Artman

(57) ABSTRACT

A radiation imaging device includes a detector capable of detecting radiation from either a KV source or an MV source. The detector includes a photodetector assembly, a scintillator adjacent to a first side of the photodetector, and a metal plate adjacent to a second side of the photodetector. The detector may also include a second scintillator. The first side of the photodetector assembly is positioned toward the KV source for KV imaging, while the second side is positioned toward the MV source for MV imaging. The radiation imaging device includes a first gantry for the MV source and a second gantry for the detector. The KV source may be supported by either the first gantry or the second gantry. The second gantry includes a robotic arm for positioning the detector for imaging, and is configured for moving the detector (and the KV source) out of the MV beam.

22 Claims, 4 Drawing Sheets

FLAT PANEL DETECTOR WITH KV/MV INTEGRATION

BACKGROUND OF THE INVENTION

The present invention relates generally to the field of radiation imaging devices, and more particularly to a flat panel detector providing Kilovolt/Megavolt (KV/MV) integration for radiation imaging devices capable of both KV imaging and MV imaging, particularly radiation imaging devices suitable for use in providing Image Guided Radiation Therapy (IGRT).

IGRT uses patient positioning devices and radiation imaging to target and treat cancerous tumors more precisely. Prior to the use of IGRT, radiation oncologists contended with variations in patient positioning, including variations caused by a patient's respiratory motion. Inevitably, a margin of healthy tissue around a treatment site was treated with radiation. However, the use of IGRT allows a radiation oncologist to determine the exact positioning of a treatment site before the administration of radiation. IGRT combines three-dimensional radiation imaging technologies including X-ray volume imaging (XVI) and the like, with intensity-modulated radiation therapy (IMRT), to treat tumors with a uniform high dose of radiation, while minimizing the amount of radiation received by surrounding tissues.

Currently, radiation imaging devices used in IGRT employ two detectors. One detector is used for capturing patient data from a KV radiation source and the second detector is used for capturing images using the MV radiation source. For example, KV imaging may be utilized for locating a treatment site, and MV imaging may be used to ensure that treatment radiation is directed to the treatment site while avoiding healthy tissue whenever possible. However, this configuration requires two photodetector assemblies (one for each radiation detector), and all of the associated hardware and electronics necessary for operating them.

Consequently, it would be desirable to provide a single detector that can be used for KV imaging as well as MV imaging without compromising image quality. Further, it would be desirable to provide a radiation imaging device having a gantry design suitable for use with this detector.

SUMMARY OF THE INVENTION

Accordingly, the present invention is directed to a detector for a radiation imaging device that is capable of detecting radiation passing through an object (e.g., the body of a patient undergoing treatment) from either a KV source or an MV source. The detector includes a photodetector assembly for detecting light emitted by a scintillator when the scintillator is excited by high energy particles emitted from the KV source or the MV source. In one embodiment of the invention, the scintillator is positioned adjacent to a first side of the photodetector assembly for receiving radiation from either the KV radiation source or the MV radiation source. A metal plate (e.g., a metal layer of brass, copper, lead, or the like) is positioned adjacent to a second side of the photodetector assembly. During KV imaging, the first side of the photodetector assembly is positioned toward the KV radiation source for receiving radiation from the KV radiation source. Similarly, during MV imaging, the second side of the photodetector assembly is positioned toward the MV radiation source for receiving radiation from the MV radiation source. In other embodiments, a second scintillator is positioned between the second side of the photodetector assembly and the metal plate for receiving radiation from the MV radiation source. In this embodiment, the first scintillator is used for KV imaging and the second scintillator is used for MV imaging.

The detector is suitable for use in a radiation imaging device that includes a first gantry for supporting the MV radiation source and a second gantry for supporting the detector. The KV radiation source may be supported by the first gantry or, alternatively, by the second gantry, and may be positioned at the same distance from the detector as the MV radiation source. The second gantry positions the first side of the photodetector assembly toward the KV beam for KV imaging and the second side of the photodetector assembly toward the MV beam for MV imaging. In embodiments where the KV radiation source is supported by the second gantry, the KV radiation source may be retracted from the path between the MV radiation source and the detector.

It is to be understood that both the foregoing general description and the following detailed description are exemplary and explanatory only and are not necessarily restrictive of the invention as claimed. The accompanying drawings, which are incorporated in and constitute a part of the specification, illustrate an embodiment of the invention and together with the general description, serve to explain the principles of the invention.

BRIEF DESCRIPTION OF THE DRAWINGS

The numerous advantages of the present invention may be better understood by those skilled in the art by reference to the accompanying figures in which.

DETAILED DESCRIPTION OF SPECIFIC EMBODIMENTS

Figure 1A:
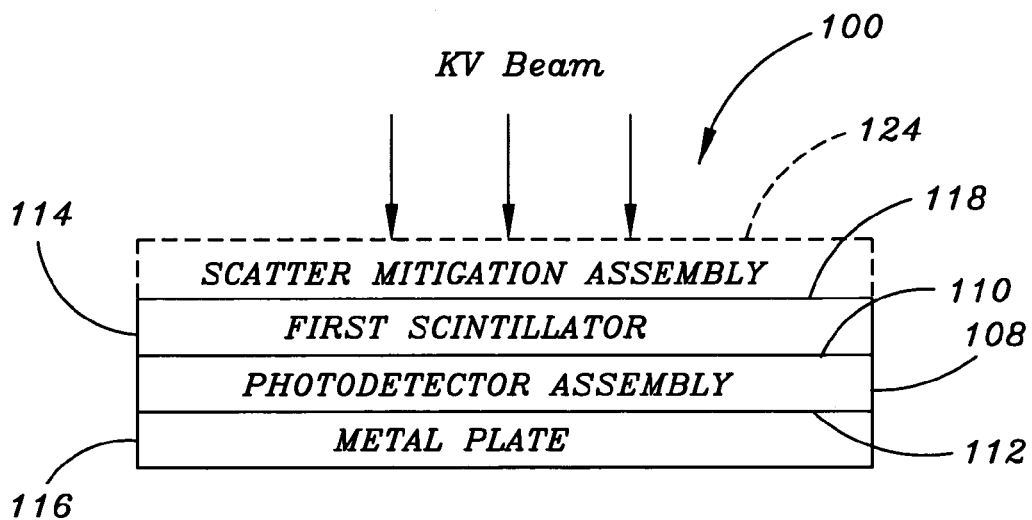
FIG. 1A is a side view of a detector capable of detecting radiation from both a KV source and an MV source, wherein the detector is positioned for detecting radiation from a KV beam in accordance with an exemplary embodiment of the present invention.
Figure 1B:
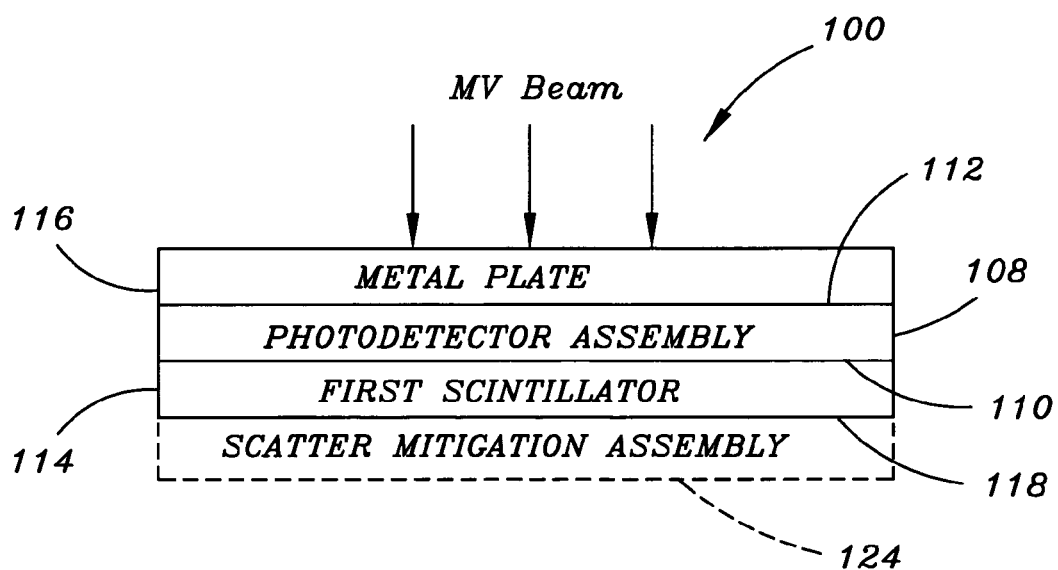
FIG. 1B is a side view of the detector illustrated in FIG. 1A, wherein the detector is positioned for detecting radiation from an MV beam.

Reference will now be made in detail to the presently preferred embodiments of the invention, examples of which are illustrated in the accompanying drawings.

Referring to FIGS. 1A through 3B, a flat panel detector 100 for a radiation imaging device, such as a radiation imaging device 102 utilized for Image Guided Radiation Therapy (IGRT), or the like, is described in accordance with exemplary embodiments of the present invention. The detector 100 may be utilized for detecting radiation from a radiation source after the radiation has passed through an object being imaged, such as a human body, or the like.

The radiation imaging device 102 includes a KV radiation source 104 for providing KV imaging and an MV radiation source 106 for providing MV imaging. The detector 100 includes a photodetector assembly 108 for detecting light, such as a burst of luminescence emitted by scintillation material along the path of a high energy particle, or the like. For example, in one embodiment, the photodetector assembly 108 comprises a number of amorphous Silicon (a-Si) photodiodes. The photodetector assembly 108 includes a first side 110 and a second side 112. A first scintillator 114, comprised of a layer of scintillation material, or the like, is positioned adjacent to the first side 110 of the photodetector assembly 108 for receiving radiation from either of the KV radiation source 104 and the MV radiation source 106, and producing light which is detectable by the photodetector assembly 108.

A metal plate 116, which attenuates radiation received from the MV radiation source 106, is positioned adjacent to the second side 112 of the photodetector assembly 108. In exemplary embodiments, the metal plate is formed of a suitable metal such as brass, copper, lead, or the like. The metal plate 116 filters low energy scatter radiation and further providing some intensification. The intensification results from high energy electrons that are generated in the metal plate, which strike phosphors or the scintillator and cause the emission of additional light photons. In accordance with the present invention, the first side 110 of the photodetector assembly 108 is positioned toward the KV radiation source 104 for receiving radiation for KV imaging, while the second side 112 of the photodetector assembly is positioned toward the MV radiation source 106 for receiving radiation for MV imaging.

The first scintillator 114 has an inner surface adjacent to the first side 110 of the photodetector assembly 108 and an outer surface 118 positioned away from the first side 110 of the photodetector assembly 108. In one specific embodiment, the outer surface 118 of the first scintillator 114 includes a reflective backing for reflecting light toward the photodetector assembly 108. Alternatively, the outer surface 118 of the first scintillator 114 includes an absorptive backing for absorbing light from the first scintillator 114. Those of skill in the art will appreciate that a reflective backing may be selected for increasing the amount of light incident upon the photodetector assembly 108 while decreasing the amount of noise in the resulting image. Further, it will be appreciated that an absorptive backing may be selected for decreasing the amount of light incident upon the photodetector assembly 108 while increasing the resolution of the resulting image. It is contemplated that a wide variety of backings may be selected for the first scintillator 114 without departing from the scope and spirit of the present invention.

Figure 2A:
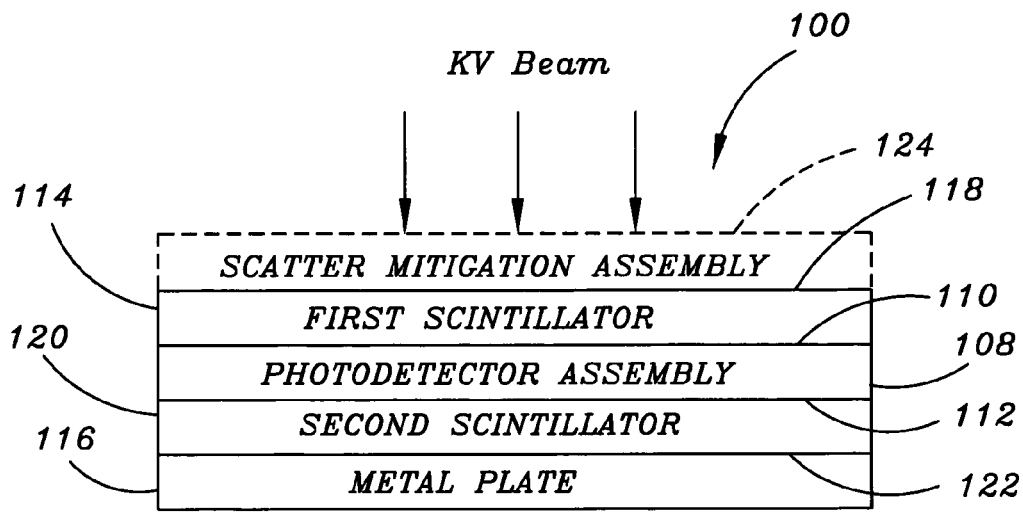
FIG. 2A is a side view of a detector capable of detecting radiation from both a KV source and an MV source, wherein the detector includes a second scintillator and is positioned for detecting radiation from a KV beam in accordance with an exemplary embodiment of the present invention.
Figure 2B:
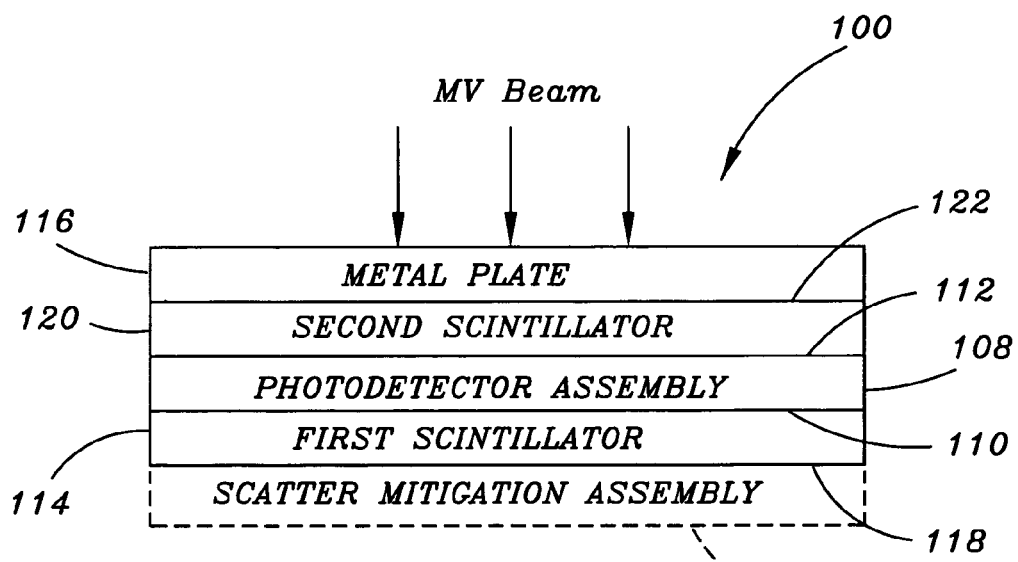
FIG. 2B is a side view of the detector illustrated in FIG. 2A, wherein the detector is positioned for detecting radiation from an MV beam.

As shown in FIGS. 2A and 2B, the detector 100 may further include a second scintillator 120, comprising a layer of scintillation material, or the like, positioned between the second side 112 of the photodetector assembly 108 and the metal plate 116, for receiving radiation from the MV radiation source 106 and producing light which is detectable by the photodetector assembly 108. It should be noted that in this configuration, the first scintillator 114 positioned adjacent to the first side 110 of the photodetector assembly 108 is primarily for receiving radiation from the KV radiation source 104. Thus, the first side 110 of the photodetector assembly 108 is positioned toward the KV radiation source 104 for receiving radiation and scintillating the first scintillator 114 for KV imaging, while the second side 112 of the photodetector assembly is positioned toward the MV radiation source 106 for receiving radiation and scintillating the second scintillator 120 for MV imaging.

The second scintillator 120 has an inner surface adjacent to the second side 112 of the photodetector assembly 108 and an outer surface 122 positioned away from the second side 112 of the photodetector assembly 108. The outer surface 122 of the second scintillator 120 is positioned adjacent to an inner surface of the metal plate 116 and away from an outer surface of the metal plate 116. In one specific embodiment, the outer surface 122 of the second scintillator 120 includes an absorptive backing for absorbing light from the second scintillator 120, while in another specific embodiment the outer surface 122 of the second scintillator 120 includes a reflective backing for reflecting light toward the photodetector assembly 108. Preferably, an absorptive backing is selected for decreasing the amount of light incident upon the photodetector assembly 108 while increasing the resolution of the resulting image. However, a reflective backing may be selected for increasing the amount of light incident upon the photodetector assembly 108 while decreasing the amount of noise in the resulting image. It is contemplated that a wide variety of backings may be selected for the second scintillator 120 without departing from the scope and spirit of the present invention.

In exemplary embodiments of the present invention shown in FIGS. 1A through 2B, the detector 100 may further include a scatter mitigation assembly 124 positioned adjacent to the outer surface 118 of the first scintillator 114. For example, the scatter mitigation assembly 124 may include a thin metal layer of brass, copper, lead, or another material for absorbing scatter radiation received from the KV radiation source 104. It is contemplated that a wide variety of materials may be selected for the scatter mitigation assembly 124 without departing from the scope and spirit of the present invention.

Figure 3A:
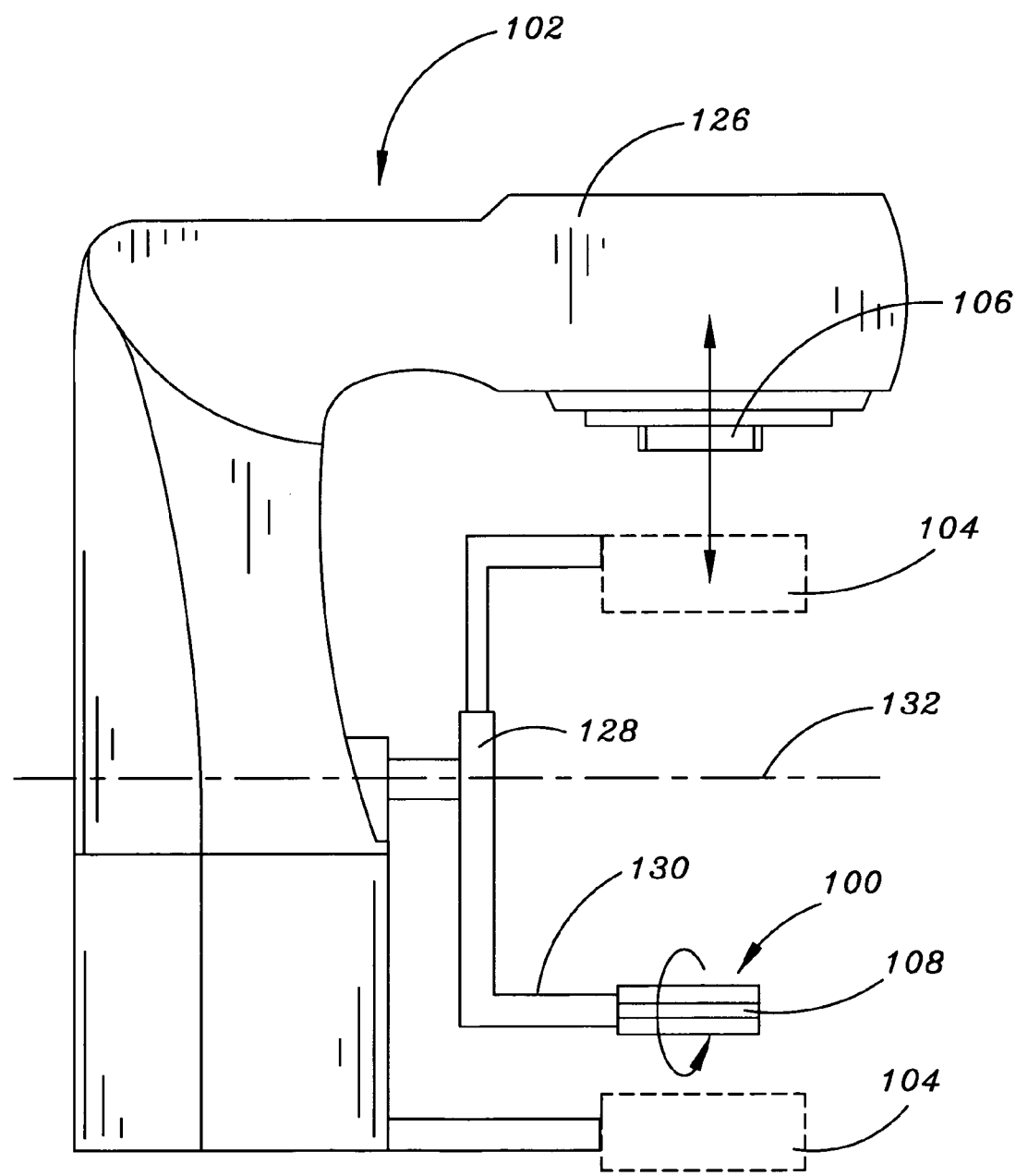
FIG. 3A is a side view of a radiation treatment device including a detector capable of detecting radiation from both a KV source and an MV source, wherein the KV source is positioned for extension to the same distance from the detector as the MV source in accordance with an exemplary embodiment of the present invention.
Figure 3B:
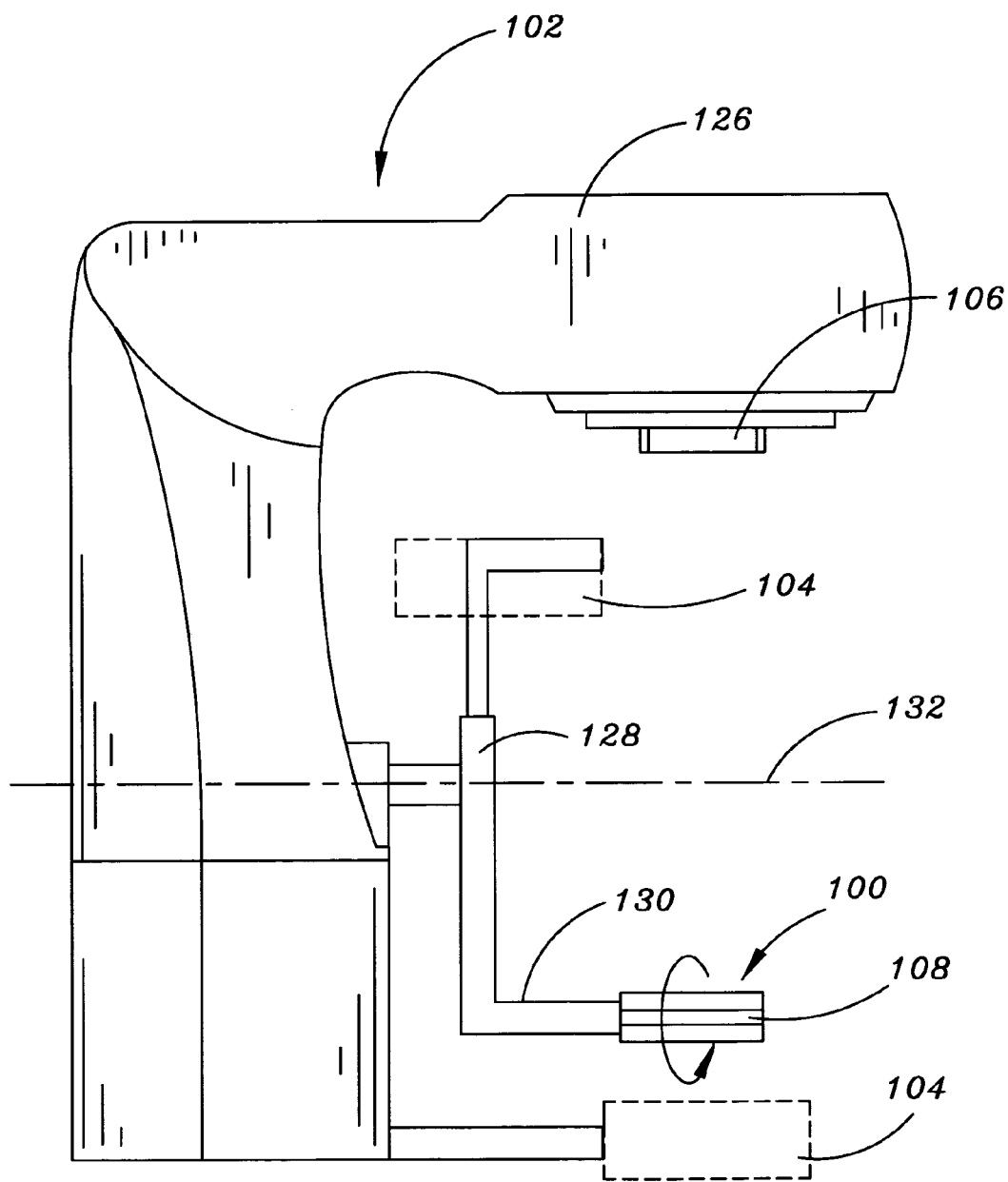
FIG. 3B is a side view of the radiation treatment device illustrated in FIG. 3A, wherein the KV source is retracted from the path of the MV source.

As shown in FIGS. 3A and 3B, the radiation imaging device 102 includes a first gantry 126 for supporting the MV radiation source 106 and a second gantry 128 for supporting the detector 100. The detector 100 is rotationally supported at an end of the second gantry 128 for being positioned in line with the MV beam so that the detector 100 is facing the MV beam. In exemplary embodiments, the second gantry 128 rotates independently of the first gantry 126 for alternately positioning the detector 100 in the path of high energy particles emitted by the MV radiation source 106, and moving the detector 100 out of the path of the MV beam. Moreover, the second gantry 128 is configured for positioning the second side 112 of the photodetector assembly 108 toward the MV radiation source 106, such as for generating MV cone beam images. For instance, in exemplary embodiments, the second gantry 128 may include a mechanical arm, a robotic arm 130, or the like, connected to the detector 100 for rotating the detector 100 so that the second side 112 of the photodetector assembly 108 faces the MV radiation source 106 for MV cone beam imaging.

In exemplary embodiments, the second gantry 128 is coaxial with the first gantry 126, having the same axis of rotation 132 as the first gantry 126. In this manner, the detector 100 may be positioned at least substantially at the same distance from the MV radiation source 106 regardless of the rotational orientation of the first gantry 126. It is contemplated that in other embodiments, the first gantry 126 and the second gantry 128 may not be coaxial, and/or the detector 100 may be positioned at different distances from the MV radiation source 106 depending upon the rotational orientation of the first gantry 126. In these embodiments, a magnification factor may be utilized for processing the MV cone beam imaging data obtained via the detector 100, such as by utilizing software, hardware, firmware, or the like, as contemplated by one of skill in the art.

The KV radiation source 104 may be supported by the first gantry 126 or, alternatively, by the second gantry 128. For example, the KV radiation source 104 and the MV radiation source 106 may be positioned across from one another and supported on opposite ends of the first gantry 126. Alternatively, the KV radiation source 104 and the MV radiation source 106 are positioned adjacent to one another and supported on one end of the first gantry 126. In a further embodiment, the detector 100 and the KV radiation source 104 are positioned across from one another and supported on opposite ends of the second gantry 128. Those of skill in the art will appreciate that the detector 100, the KV radiation source 104, and the MV radiation source 106 may be positioned in a variety of ways without departing from the scope and intent of the present invention.

Preferably, the KV radiation source 104 and the MV radiation source 106 are capable of being positioned at least substantially at the same distance from a target toward which high energy particles emitted by the KV radiation source 104 and the MV radiation source 106 are directed. That is, the KV radiation source 104 should be capable of attaining the same "eye view" of a target location as the MV radiation source 106. For example, in one specific embodiment, the KV radiation source 104 and the MV radiation source 106 may be positioned for the same eye view of the detector 100 when the detector 100 is placed in line with either of the KV radiation source 104 and the MV radiation source 106.

Those of skill in the art will appreciate that in exemplary embodiments of the present invention in which the detector 100 and the KV radiation source 104 are positioned across from one another and supported on opposite ends of the second gantry 128, the KV radiation source 104 may be positioned in a first position at least substantially at the same distance from the detector 100 as the MV radiation source 106, and in a second position retracted from the path between the MV radiation source 106 and the detector 100. In this manner the second gantry 128 provides for adjustment of the distance between the KV radiation source 104 and the detector 100 so that the distance between the KV imaging source and the detector during KV imaging is equal to the distance between the MV radiation source 106 and the detector 100 during MV imaging.

In exemplary embodiments, the robotic arm 130 connected to the detector 100 is configured for rotating the detector 100 so that the first side 110 of the photodetector assembly 108 faces the KV radiation source 104 for KV cone beam imaging. It is contemplated that in some embodiments, the detector 100 may be positioned at different distances from the KV radiation source 104 depending upon the orientation of the KV radiation source 104 and the second gantry 128. In these embodiments, a magnification factor may be utilized for processing the KV cone beam imaging data obtained via the detector 100, such as by utilizing software, hardware, firmware, or the like, as contemplated by one of skill in the art.

It should be noted that the detector 100 may be configured for multiple electronics gain for either of a KV imaging mode and an MV imaging mode. For instance, the detector 100 may apply an appropriate electronics gain to avoid detector saturation, or the like. Further, in exemplary embodiments, all readout electronics relating to the detector 100 are placed outside of the MV radiation field.

It is believed that the present invention and many of its attendant advantages will be understood by the foregoing description, and it will be apparent that various changes may be made in the form, construction and arrangement of the components thereof without departing from the scope and spirit of the invention or without sacrificing all of its material advantages. The form herein before described being merely an explanatory embodiment thereof, it is the intention of the following claims to encompass and include such changes.

What is claimed is:

1. A detector for a radiation imaging device having at least one of a KV radiation source for providing KV imaging and an MV radiation source for providing MV imaging, comprising:
    a photodetector assembly for detecting light, the photodetector assembly having a first side and a second side;
    a scintillator disposed adjacent to the first side of the photodetector assembly for receiving radiation and producing light detectable by the photodetector assembly; and
    a metal plate disposed adjacent to the second side of the photodetector assembly for attenuating radiation having an energy in the megavolt (MV) range,
    wherein the first side of the photodetector assembly is positioned toward the KV radiation source for KV imaging and the second side of the photodetector assembly is positioned toward the MV radiation source for MV imaging.

2. The detector as claimed in claim 1, wherein the scintillator has an inner surface disposed adjacent to the first side of the photodetector assembly and an outer surface having a reflective backing for reflecting light toward the photodetector assembly.

3. The detector as claimed in claim 1, further comprising a second scintillator disposed between the second side of the photodetector assembly and the metal plate for receiving radiation and producing light detectable by the photodetector assembly, the first scintillator for receiving radiation having an energy in the kilovolt (KV) range and the second scintillator being optimized for receiving radiation having an energy in the megavolt (MV) range.

4. The detector as claimed in claim 3, wherein the metal plate has an inner surface and an outer surface, and the second scintillator has an inner surface disposed adjacent to the second side of the photodetector assembly and an outer surface disposed adjacent to the inner surface of the metal plate, the outer surface of the second scintillator including an absorptive backing for absorbing light produced by the second scintillator.

5. The detector as claimed in claim 3, wherein the metal plate has an inner surface and an outer surface, and the second scintillator has an inner surface disposed adjacent to the second side of the photodetector assembly and an outer surface disposed adjacent to the inner surface of the metal plate, the outer surface of the second scintillator including a reflective backing for reflecting light produced by the second scintillator to the photodetector assembly.

6. The detector as claimed in claim 1, further comprising a scatter mitigation assembly disposed adjacent to an outer surface of the scintillator for mitigating scatter of radiation having an energy in the kilovolt (KV) range.

7. The detector as claimed in claim 6, wherein the scatter mitigation assembly comprises a metal layer.

8. The detector as claimed in claim 1, wherein the photodetector assembly comprises a plurality of amorphous Silicon (a-Si) photodiodes.

9. The detector as claimed in claim 1, wherein the metal plate comprises a metal selected from the group of copper, brass and lead.

10. A radiation imaging device, comprising:
a KV radiation source for emitting radiation having an energy in the kilovolt (KV) range for KV imaging;
an MV radiation source for emitting radiation having an energy in the megavolt (MV) range for MV imaging;
a detector for detecting radiation from the KV radiation source and the MV radiation source after the radiation has passed through an object being imaged, the detector having a first surface for receiving radiation from the KV radiation source and a second surface opposite the first surface for receiving radiation from the MV radiation source,
wherein for MV imaging the first surface of the detector is positioned toward the MV radiation source and for KV imaging the second surface of the detector is positioned toward the KV radiation source.

11. The radiation imaging device as claimed in claim 10, wherein the detector comprises:
a photodetector assembly for detecting light, the photodetector assembly having a first side and a second side;
a scintillator disposed adjacent to the first side of the photodetector assembly for receiving radiation and producing light detectable by the photodetector assembly; and
a metal plate disposed adjacent to the second side of the photodetector assembly for attenuating radiation having an energy in the megavolt (MV) range,
wherein the first side of the photodetector assembly is positioned toward the KV radiation source for KV imaging and the second side of the photodetector assembly is positioned toward the MV radiation source for MV imaging.

12. The radiation imaging device as claimed in claim 11, wherein the scintillator has an inner surface disposed adjacent to the first side of the photodetector assembly and an outer surface having a reflective backing for reflecting light toward the photodetector assembly.

13. The radiation imaging device as claimed in claim 11, further comprising a second scintillator disposed between the second side of the photodetector assembly and the metal plate for receiving radiation and producing light detectable by the photodetector assembly, the first scintillator for receiving radiation having an energy in the kilovolt (KV) range and the second scintillator being optimized for receiving radiation having an energy in the megavolt (MV) range.

14. The radiation imaging device as claimed in claim 13, wherein the metal plate has an inner surface and an outer surface, and the second scintillator has an inner surface disposed adjacent to the second side of the photodetector assembly and an outer surface disposed adjacent to the inner surface of the metal plate, the outer surface of the second scintillator including an absorptive backing for absorbing light produced by the second scintillator.

15. The radiation imaging device as claimed in claim 13, wherein the metal plate has an inner surface and an outer surface, and the second scintillator has an inner surface disposed adjacent to the second side of the photodetector assembly and an outer surface disposed adjacent to the inner surface of the metal plate, the outer surface of the second scintillator including a reflective backing for reflecting light produced by the second scintillator to the photodetector assembly.

16. The radiation imaging device as claimed in claim 11, further comprising a scatter mitigation assembly disposed adjacent to an outer surface of the scintillator for mitigating scatter of radiation having an energy in the kilovolt (KV) range.

17. The radiation imaging device as claimed in claim 10, further comprising a first gantry for supporting the MV radiation source and a second gantry coaxial with the first gantry for supporting the detector, the second gantry providing for rotation of the detector for positioning the detector.

18. The radiation imaging device as claimed in claim 17, wherein the second gantry comprises a robotic arm for rotating the detector.

19. The radiation imaging device as claimed in claim 17, wherein the first gantry further supports the KV radiation source.

20. The radiation imaging device as claimed in claim 17, wherein the second gantry further supports the KV radiation source, the second gantry providing for retraction of the KV radiation source from the radiation emitted by the MV radiation source during MV imaging.

21. The radiation imaging device as claimed in claim 20, wherein the second gantry further provides adjustment of the distance between the KV imaging source and the detector so that the distance between the KV imaging source and the detector during KV imaging is equal to the distance between the MV radiation source and the detector during MV imaging.

22. A detector for a radiation imaging device having at least one of a KV radiation source for providing KV imaging and an MV radiation source for providing MV imaging, comprising
means for detecting light, the light detecting means having a first side and a second side;
means, disposed adjacent to the first side of the light detecting means, for receiving radiation and producing light detectable by the light detecting means; and
means, disposed adjacent to the second surface of the light detecting means, for attenuating radiation having an energy in the megavolt (MV) range,
wherein the first side of the light detecting means is positioned toward the MV radiation source for MV imaging and the second side of the light detecting means is positioned toward a KV radiation source for KV imaging.

* * * * *